United States Patent [19]

Mieville

[11] 4,179,515

[45] Dec. 18, 1979

[54] BENZOYLPHENOXY PROPIONIC ACID, ESTERS THEREOF AND PHARMACEUTICAL COMPOSITION

[75] Inventor: André Mieville, Lausanne, Switzerland

[73] Assignee: Orchimed S. A., Switzerland

[21] Appl. No.: 846,323

[22] Filed: Oct. 28, 1977

Related U.S. Application Data

[62] Division of Ser. No. 656,711, Feb. 9, 1976, Pat. No. 4,072,705.

[30] Foreign Application Priority Data

Feb. 12, 1975 [GB] United Kingdom ............... 5979/75
Dec. 10, 1975 [GB] United Kingdom ............. 50630/75

[51] Int. Cl.² .................. A61K 31/335; C07C 69/95
[52] U.S. Cl. ........................... 424/278; 260/340.9 R;
424/308; 424/309; 424/317; 424/319; 560/21;
560/48; 560/52; 562/436; 562/441; 562/460
[58] Field of Search ................... 560/21, 52, 61, 62,
560/36, 48; 562/435, 436, 441, 471, 472, 460;
424/308, 309, 278, 317, 319; 260/340.9 R

[56] References Cited

U.S. PATENT DOCUMENTS

| | | | |
|---|---|---|---|
| 3,332,842 | 7/1967 | Bencze | 424/317 X |
| 3,332,957 | 7/1967 | Bencze | 424/317 X |
| 3,383,411 | 5/1968 | Schultz et al. | 560/21 X |
| 3,445,511 | 5/1969 | Cragoe | 424/317 X |
| 3,704,314 | 11/1972 | Cragoe et al. | 424/308 X |
| 3,755,603 | 8/1973 | Harrison et al. | 424/317 X |

FOREIGN PATENT DOCUMENTS

2356655 5/1974 Fed. Rep. of Germany ............. 560/61

*Primary Examiner*—Bernard Helfin
*Assistant Examiner*—Vera C. Clarke
*Attorney, Agent, or Firm*—Bacon & Thomas

[57] ABSTRACT

Compounds of the formula

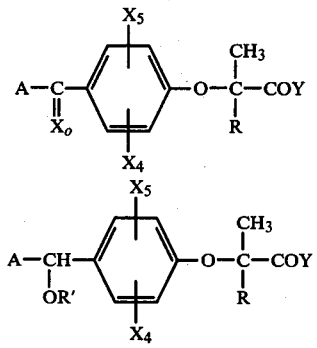

in which A is lower alkyl, or a substituted or unsubstituted phenyl, thienyl, furyl, indolyl or thiaindolyl radical, R, $X_4$ and $X_5$ are hydrogen or lower alkyl, Y is hydrogen, hydroxy, etherified hydroxy, substituted amino, or N-attached heterocyclyl, $X_0$ is O or $OCH_2C-H_2O$, R′ represents hydrogen, lower alkyl or acetyl; and acid-addition salts thereof, are novel and useful in pharmacy as hypolipaemiant, hypocholosterolaemiant and cholagogic agents or in the preparation of such agents.

6 Claims, No Drawings

BENZOYLPHENOXY PROPIONIC ACID, ESTERS THEREOF AND PHARMACEUTICAL COMPOSITION

This is a division, of application Ser. No. 656,711, filed Feb. 9, 1976, now U.S. Pat. No. 4,072,705.

The present invention relates to industrial products which are particularly useful in therapeutics as active medicaments in the cardiovascular field, in particular as hypolipidaemiant, hypocholesterolaemiant and cholagogic agents. It also relates to processes for synthesising these products and their application in therapeutics.

More especially, the invention is directed to:

(1) the compounds of formula II hereinafter, which are new industrial products useful in therapeutics;

(2) the compounds of formula I hereinafter, which are particularly involved as intermediates in the synthesis of the compounds of formula II and which are also useful in therapeutics, and except for some products already described in French Patent Nos. 2 035 821 and 2 157 853, the compounds of formula I are new products;

(3) the new processes for synthesising compounds of formula I and II; and (4) the therapeutic application of the new compounds I and II, particularly as hypolipidaemiant, hypocholesterolaemiant and cholagogic agents.

According to the invention the following acids are proposed: p-(alkyl-carbonyl)-, p-(cycloalkyl-carbonyl), p-(aryl-carbonyl)-, p-(heteroarylcarbonyl)-, p-[α-alkyl-α-hydroxy)methyl], p-[(4-cycloalkyl-α-hydroxy)-methyl], p-[(α-aryl-α-hydroxy]methyl)- and p-(heteroaryl-α-hydroxy)methyl)-phenoxyalkylcarboxylic acids and their derivatives (in particular the derivatives which result from (i) esterification and amidification of the carboxylic acid group, and (ii) esterification and etherification of the α-hydroxy group on the one hand, or conversion of the p-carbonyl group to the acetal group on the other hand), which have the following formulae:

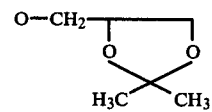   I

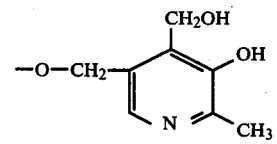   II in which A represents methyl, ethyl, n-propyl, isopropyl, n-butyl

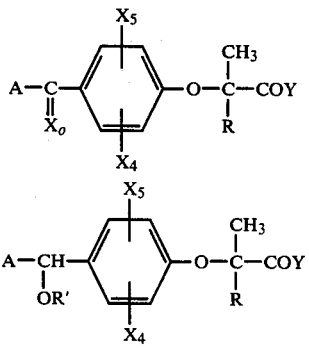

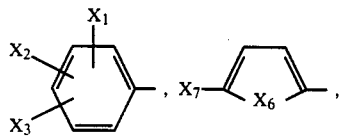

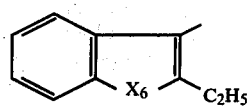

[where $X_1$, $X_2$ and $X_3$ are the same or different and each represents, H, Cl, Br, F, $CF_3$, $NO_2$, $NH_2$, OH, $C_{1-4}$ alkyl group, $C_{1-4}$ alkoxy group, benzyloxy group, acetylamino group, acetoxy group, CHO, COOH, $OC(CH_3)_2COY_1$ (where $Y_1$ is preferably OH or $C_{1-4}$ alkoxy); $X_6$ represents O or S; and $X_7$ represents H, Cl, Br]; R, $X_4$ and $X_5$, which are identical or different, each represents a hydrogen atom or a $C_{1-4}$ alkyl group; $X_0$ is O or $OCH_2CH_2O$, Y represents H, OH, OM (where M is a metal or a stoichiometric portion of a metal), a $C_{1-12}$ alkoxy group (whose hydrocarbon radical is straight-chain or branched), a $C_{3-8}$ cycloalkyloxy group, a $C_{1-4}$ alkylthio group, a 2,3-dihydroxypropyloxy group, a 4-(2,2-dimethyl-1,3-dioxolanyl)-methyleneoxy group, which is derived from the preceding group and has the formula:

$$O-CH_2-\underset{\underset{H_3C}{\overset{O}{|}}\underset{CH_3}{\overset{O}{|}}}{\bigvee}$$

a phenoxy group, a substituted phenoxy group (particularly a p-chlorophenoxy group), a 3-pyridyl-methyleneoxy group, a 5-(2-methyl-3-hydroxy-4-hydroxymethylpyridyl)-methyleneoxy group, which has the formula:

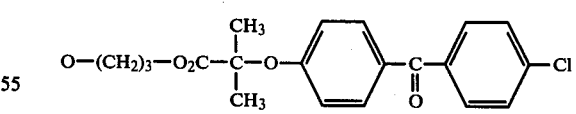

a $NZ_1Z_2$, $NHCH_2CH_2NZ_1Z_2$, $OCH_2CH_2NZ_1Z_2$ or $O(CH_2)mCONZ_1Z_2$ group (where m is an integer from 1 to 4 and $Z_1$ and $Z_2$ are $C_{1-4}$ alkyl groups, and $Z_1$ and $Z_2$ together with the nitrogen atom to which they are joined may form a 5- to 7-membered N-heterocyclic group which may contain a second heteroatom such as O and N and may be substituted), or a group $$O-(CH_2)_3-O_2C-\underset{\underset{CH_3}{|}}{\overset{\overset{CH_3}{|}}{C}}-O-\langle\;\rangle-\underset{\underset{O}{\|}}{C}-\langle\;\rangle-Cl$$

R' represents hydrogen, a $C_{1-4}$ alkyl group or an acetyl group; and their addition salts.

Examples of the metal represented by M are Na, K, ½Ca, ½Mg, ½Zn, and ⅓Al, preferably Na or K.

The alkyl, alkoxy and alkylthio groups in the compounds according to the invention contain a straight-chain or branched hydrocarbon radical. Among the $C_{1-4}$ alkyl groups, the methyl group is preferred for $X_1$, $X_2$, $X_3$, $X_4$, $X_5$, R and R' is methyl, while hydrogen, methyl, ethyl, isopropyl and n-butyl are preferred for $Z_1$ and $Z_2$.

The $C_{1-12}$ alkoxy groups include the following preferred groups: methoxy, ethoxy, isopropyloxy, isobutyloxy, tert.butyloxy, 1-octyloxy, 1-dodecyloxy, 2-pentyloxy and 3-pentyloxy.

The $C_{3-8}$ cycloalkyloxy groups preferred are the cyclopentyloxy, cyclohexyloxy and cyclooctyloxy groups.

Of the 5- to 7-membered N-heterocyclic $NZ_1Z_2$ groups, which are optionally substituted, the pyrrolidino, morpholino, piperidino, 4-methylpiperidino, 4-methylpiperazino, 4-phenylpiperazino, 4-p-chlorophenyl-piperazino and hexamethyleneimino groups are particularly intended.

Of the Y-groups containing at least one nitrogen atom, the preferred groups for $Y=NZ_1Z_2$ are the $N(CH_3)_2$, $N(C_2H_5)_2$, $N(n-C_4H_9)$, piperidino and morpholino groups; the preferred groups for $Y=NHCH_2CH_2NZ_1Z_2$ are the 2-dimethylaminoethylamino and 2-diethylamino-ethylamino groups; the preferred groups for $Y=OCH_2CH_2NZ_1Z_2$ are the hexamethyleneiminoethoxy, morpholinoethoxy, piperidinoethoxy and 2-diethylaminoethoxy groups.

By the term addition salts are understood the ammonium salts and acid-addition salts obtained with the compounds of formulae I and II which have at least one amino group. The acid addition salts may be prepared by reacting the base with a mineral or organic acid, particularly with hydrochloric, fumaric, maleic and oxalic acids.

Various methods for synthesising the compounds I and II and their intermediates are given hereinafter. These methods which relate to compounds where A=-substituted phenyl can of course be directly transferred to compounds where A=heteroaryl.

The products prepared in accordance with these methods are given in Tables I, II and III hereinafter.

Some of the hydroxyketone intermediate compounds formed in the synthesis of compounds in accordance with the present invention have been set out in Table IV.

In accordance with the invention there are provided therapeutically useful compositions, particularly for the treatment of hyperlipaemia and containing as active ingredient a pharmaceutically active quantity of at least one compound of formula I or II or a non-toxic acid addition salt thereof, in association with a physiologically acceptable excipient.

The compounds of formula II are obtained:

(1) From compounds of formula I according to the reaction scheme I as follows:

REACTION SCHEME I

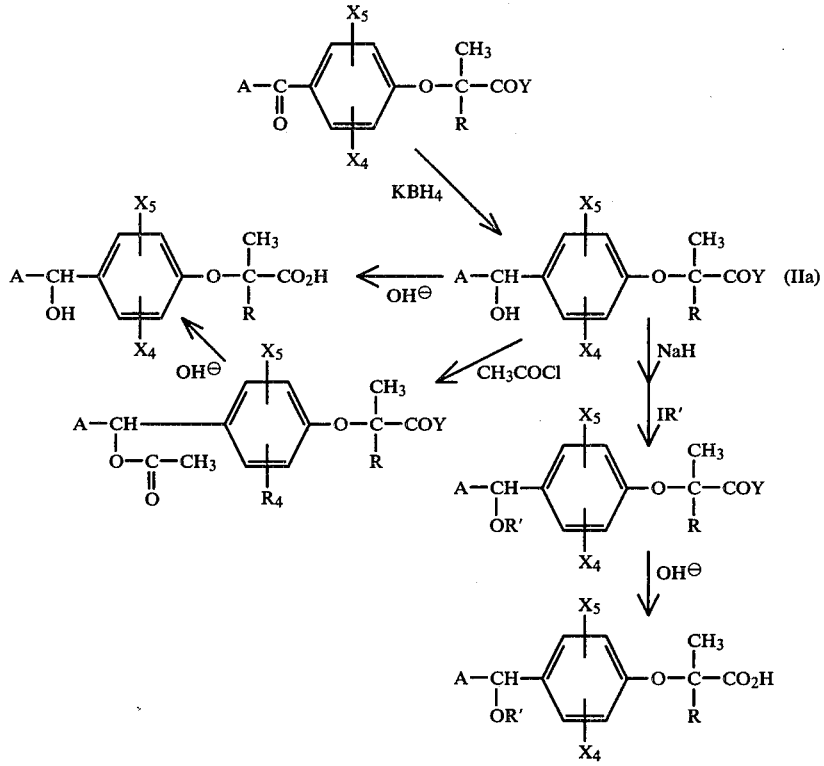

The following comments may be made concerning this reaction scheme:

(a) the step I→IIa is preferentially effected using potassium borohydride, but it is also possible to use a metal isopropylate.

(b) if A is

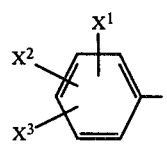

and (i) $X_1$, $X_2$ or $X_3=NO_2$, the reducing medium (step I→IIa) affects this $NO_2$ group; this type of compound should therefore be prepared by a method which produces an alcohol group in a non-reducing medium (corresponds to item 2 under preparation of (4'-chlorophenyl)-(2-phenoxy-2-methylpropionic acid) carbinol).

(ii) $X_1$, $X_2$ or $X_3=OH$ or $NH_2$, the compounds II in which R'=alkyl and acetyl are obtained indirectly; the OH or $NH_2$ group should in fact be introduced last of all via a $NO_2$ group: the step $NO_2 \rightarrow OH$ is effected by a process known per se; the step $NO_2 \rightarrow NH_2$ is effected by catalytic reduction.

EXAMPLE

Preparation of (4'-chlorophenyl)-(2-phenoxy-2-methylpropionic acid isopropyl ester) carbinol (alternative name isopropyl 2-[4-(p-chloro-α-hydroxybenzyl)-phenoxy]-2-methyl propionate)

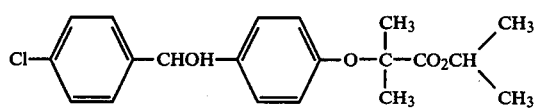

350 g of isopropyl 2-[4-(p-chlorobenzoyl)-phenoxy]-2-methylpropionate is dissolved in 4200 cm' of methanol in an Erlenmeyer flask, 60 g of $KBH_4$ is added and the mixture is stirred for 8 hours at ambient temperature; the methanol is then evaporated and the residue is taken up in water and methylene chloride; the organic phase is washed with water until neutral and then dried, and the methylene chloride is evaporated in vacuo; the remaining very clear oily residue is almost always very pure and may be used for any purpose; the yield is quantitative; (if a small amount of the initial ketone remains this can easily be removed simply by treating if with Girard's T reagent). $N_D^{20} = 1.5428$ Preparation of (4'-chlorophenyl)-(2-phenoxy-2-methylpropionic acid) carbinol A conventional hydrolysis in 4 N NaOH for 6 hours at 80°–85° C. gives the expected acid-alcohol:
Yield: 95%
m.p.=132° C.

(2) Directly without proceeding via a ketone

In this process one of the techniques for obtaining compounds of structure I is used—see section Ab3 hereinafter; this is the method which is especially preferred to obtain compounds II where $X_1$, $X_2$ or $X_3 = NO_2$.

(3) According to a special process, shown in reaction scheme II as follows.

REACTION SCHEME II

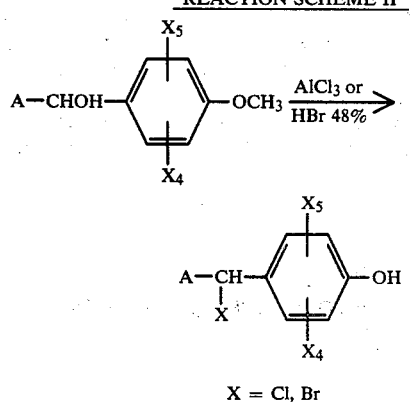

X = Cl, Br

-continued
REACTION SCHEME II

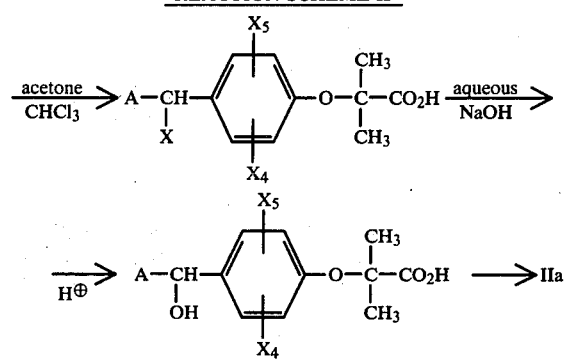

All the stages in reaction scheme II are conventional. However, this particular reaction mechanism is unsuitable for synthesising alcohols IIa where $X_1$, $X_2$ or $X_3 = NH_2$, OH, $CF_3$ or alkoxy.

The methods dealing with the synthesis of compounds of formula I are summarised hereinafter.

A—DIRECT ACCESS TO COMPOUNDS OF FORMULA I a—Methods employing a Friedel-Crafts reaction Method Aa1:

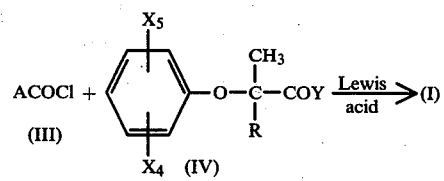

The two industrial or known reactants III and IV are reacted in a solvent which is particularly suitable for carrying out a Friedel-Crafts reaction (carbon disulphide, dichloroethane, benzene, methylene chloride, nitrobenzene, nitromethane, compound IV itself). The catalyst is a Lewis acid selected from aluminum chloride, tin tetrachloride, titanium tetrachloride, boron trifluoride and antimony pentafluoride. This latter compound ($SbF_5$) must definitely be used to carry out the reaction when one of the substituents $X_1$, $X_2$ or $X_3$ is the radical $CF_3$.

If one of the substituents $X_1$, $X_2$ or $X_3$ is $NH_2$ or OH, this method may not be used directly, and it is necessary either to protect these groups via acetyl in the form

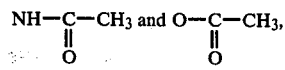

or carry out the Friedel-Crafts reaction on a compound III bearing a group which will readily produce $NH_2$ and OH, for example a $NO_2$ group. Since the step $NO_2 \rightarrow NH_2$ is a conventional reduction, the step $NO_2 \rightarrow OH$ may be carried out directly in accordance with a process known per se.

As regards the substituents Y in compound IV which enable this type of reaction to be carried out, the preferred are $OCH_3$ and $OC_2H_5$, while the OH group should be excluded.

METHOD Aa2

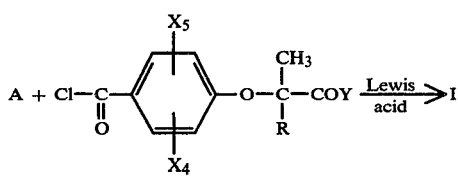

All the comments in the preceding paragraph apply equally in this case and should be observed in exactly the same manner when performing this reaction scheme, which relates solely to compounds in which A is aryl or heteroaryl.

As regards the compound

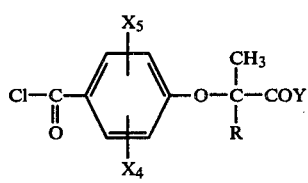

this is obtained in a conventional manner according to one of the following reaction pathways:

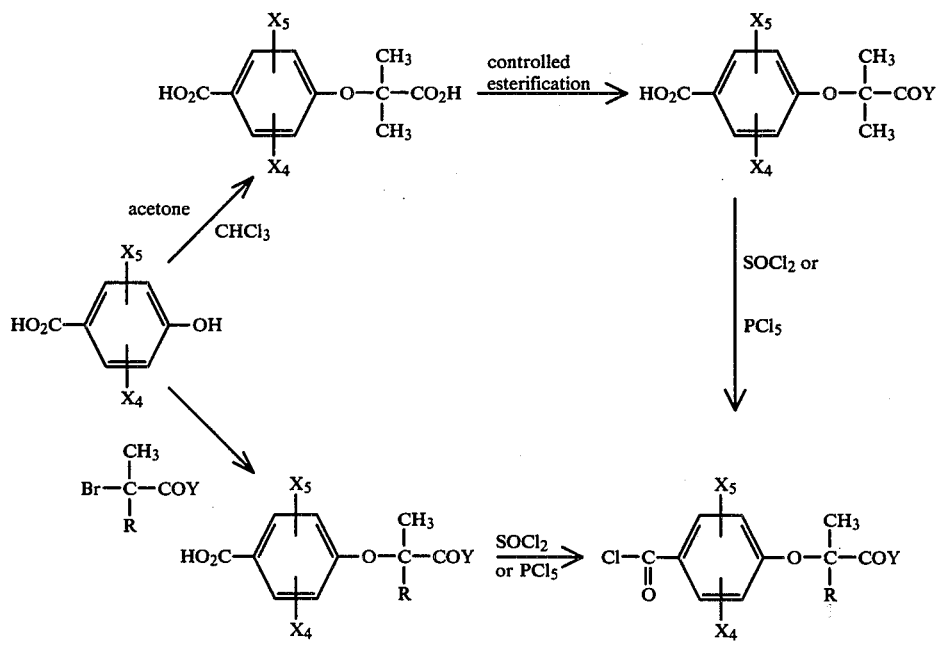

b—Processes employing an organo-magnesium compound

These processes in fact utilise the property of organo-magnesium compounds by which they give ketones when reacted with a nitrile or acid chloride: ketones I will thus be obtained; if the same organo-magnesium compound is reacted not with a nitrile or acid chloride but with an aldehyde, an alcohol of formula II is directly obtained.

METHOD Ab1 use of a nitrile

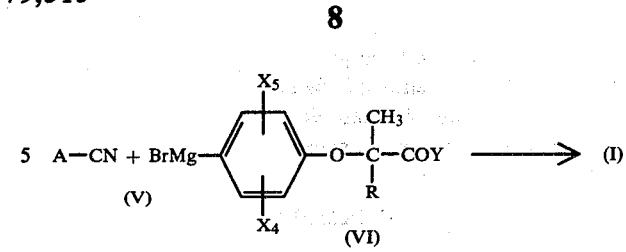

The condensation is carried out at a temperature between $-10°$ C. and $+30°$ C. in the solvent which was used to prepare the organo-magnesium compound VI (ether or THF). This organo-magnesium compound VI may in all cases be prepared from

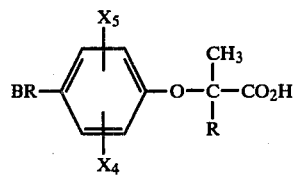

after salifying the acid group with NaOH(Y=ONa) or, better, by $CH_3MgI$ or $C_2H_5MgBr$ (Y=OMgI, OMgBr respectively).

The preparation of the organo-magnesium compound properly speaking: Br→MgBr, is effected by reacting the bromine derivative thus protected with magnesium, in ether or anhydrous THF. However, it is preferable to carry out the two operations in one to prepare the "dimagnesium" compound VIa by exchange with $CH_3MgI$.

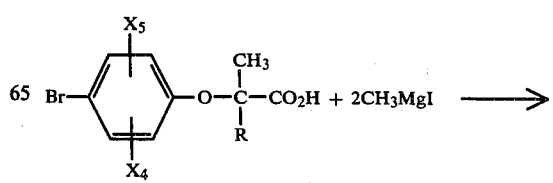

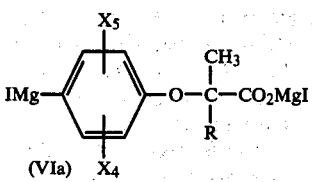

Example illustrating this method

Preparation of 2-[(para-benzyl)-phenoxy]-2-methyl-propionic acid 26 g (0.1 mole) of 2-[(para-bromo)-phenoxy]-2-methyl-propionic acid is dissolved in 200 cc of anhydrous THF and placed in a 500 cc flask. The mixture is cooled in an ice bath and 0.2 mole of methylmagnesium iodide (prepared in solution of THF) is added slowly. After this addition, the temperature is allowed to rise and the mixture stirred at ambient temperature for 1½ hours. Then slowly and drop by drop a solution of 4.1 g (0.1 mole) of benzonitrile in 20 cc of THF is added and the mixture is stirred for 2 hours 30 minutes at ambient temperature. The reaction mixture is poured on to 500 cc of 10% hydrochloric acid, cooled by 500 g of ice, and vigorously stirred. The reaction mixture is extracted with ether and the ethereal phases are washed, dried and decolorised. The ether solvent is evaporated under vacuum and the oily residue placed in a desiccator under vacuum. 2-[(para-benzoyl)-phenoxy]-2-methylpropionic acid slowly crystallises (22 g). The yield is 77% and the melting point 130° C.

Method Ab2

Use of an acid chloride

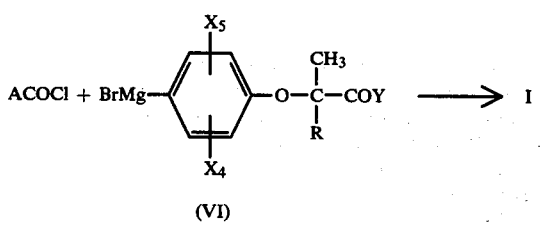

In this case the condensation is carried out at a lower temperature (between −30° C. and +10° C.), care being taken to see that the acid chloride is never in excess (it is the acid chloride which will be added to the organo-magnesium compound).

On the other hand, the use of a copper halide (CuBr, CuCl, CuI) which is reacted with VI (mole per mole) before adding the acid chloride very often gives better yields. The preparation of VI is carried out as mentioned above.

Non-limiting Example

Preparation of 2-[(para-4′-fluorobenzoyl)-phenoxy]-2-methyl-propionic acid 0.1 mole of dimagnesium halide of formula

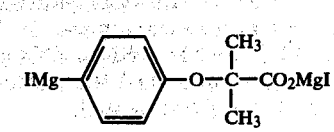

is prepared in a 500 cc flask by the method described above. The reaction mixture is cooled to −25° C. and 19 g (0.1 mole) of cuprous iodide is added. A solution of 10.7 g (0.1 mole) of p-fluorobenzoyl chloride in 50 cc of THF is added drop by drop over half-an-hour through a dropping funnel. The temperature is then allowed to rise to 15° to 20° C. and the mixture poured on to 500 cc of 10% of HCl and 500 g of ice. After extraction with ether, and washing, drying and decolorisation of the ethereal phases, the solvent is evaporated under vacuum to give a solid residue of the desired acid. Yield 20 g (68%), melting point 160° C.

Method Ab3

Use of an aldehyde

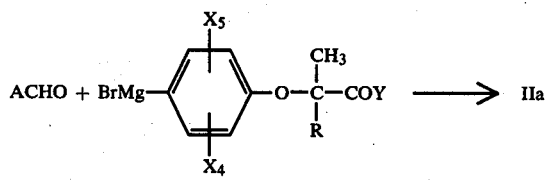

The condensation is carried out at a temperature between −10° C. and +30° C., in the solvent which was used in the preparation of the organo-magnesium compound VI (ether of THF). As regards VI compounds, it is obtained as described above.

Non-limiting Example

Preparation of 2-[p-(α-para-nitrobenzyl-α-hydroxy)-methyl]-phenoxy-2-methyl propionic acid

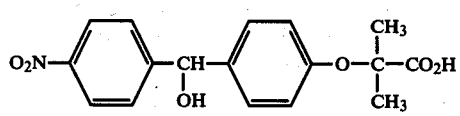

0.1 mole of the dimagnesium halide is prepared in a 500 cc flask as described above. The reaction mixture is cooled in an ice bath and at that temperature a solution of 15 g (0.1 mole) of p-nitrobenzaldehyde in 30 cc of THF is added slowly. The mixture is allowed to return to ambient temperature over a period of 2 hours whereupon it is hydrolysed and treated as described above. The desired acid alcohol produced is a solid melting at 148° C. Yield 71 g (64%).

These methods Ab1, Ab2 or Ab3 do not ensure direct access to compounds I or II when A is

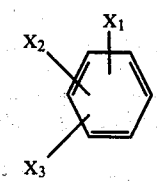

where $X_1$, $X_2$ or $X_3$ are incompatible with a reaction involving organo-magnesium compounds. This is also the case where $X_1$, $X_2$ or $X_3 = NH_2$ and OH; in this case the compounds of formula I and II are obtained via $X_1$, $X_2$ or $X_3 = NO_2$ as described in Aa1.

c-processes using a phenol

Direct access to the isobutyric acid group

There are three possibilities, which are summarised in the following reaction scheme:

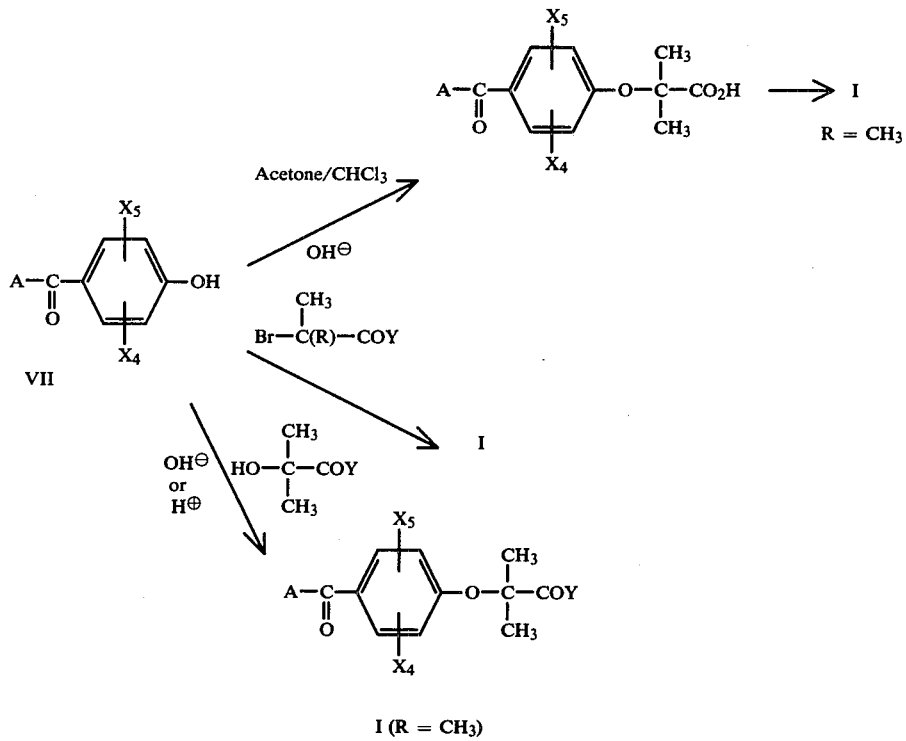

I (R = CH$_3$)

Method Ac1 employing "acetone-chloroform" is preferred when R=CH$_3$, since it gives good yields; A slight modification to the method may be made, by isolating as an intermediate the acetone+chloroform reaction product, namely

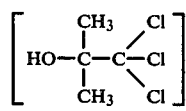

and reacting this compound with the hydroxyketone VII in alkaline medium.

EXAMPLE

Preparation of
2-(4-(p-chlorobenzoyl)-phenoxy)-2-methylpropionic acid 12 l of anhydrous acetone, 1.395 kg (6 moles) of 4-chloro-4-hydroxybenzophenone and 1.44 kg (6 moles) of soda are placed in a 20-liter flask; the reaction mixture is heated 1 to 2 hours under reflux to form the phenate, the source of heat is removed, and a mixture of 2.16 kg of chloroform (18 moles) diluted in 3.5 liters of acetone is then added.

The addition of the mixture is sufficient to maintain reflux for at least 6 hours; after 4 hours (when one-quarter of the mixture remains to be added) the exothermicity of the reaction decreases, and heating is recommenced to maintain the reflux for 6 to 8 hours after the end of the addition; the mixture is allowed to cool and the sodium chloride which has precipitated is filtered off (the sodium salt of the desired acid is dissolved in the acetone); the acetone is evaporated in vacuo and the residue is dissolved in the minimum amount of lukewarm water (approximately 35° C.); this aqueous phase is washed very carefully with dichloroethane (3-4 times) and is then acidified to a pH-value of 1 by HCl while cooling, whereupon the acid precipitates; the reaction mixture is shaken vigorously, and after 30 minutes this acid is suction-dried, washed with copious amounts of water and then dried.

Weight=1.61 kg;
m.p.=182° C.;
Yield: 85%

This acid contains a few traces (3 to 4%) of unreacted phenol, but since all the other impurities have been able to be eliminated by means of this simple treatment it would be quite pointless to carry out purification of this acid with sodium bicarbonate (this is industrially very beneficial).

To obtain the acid pure as such, it is recrystallised in toluene; m.p.=185° C.

Method Ac2 employing

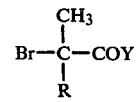

(the bromine may be replaced by Cl or I) is particularly preferred when R=H or when one of the substituents $X_1$, $X_2$ or $X_3$ of the group A is $NO_2$ or $CF_3$. This condensation is carried out in ethyl alcohol or isobutyl methyl ketone in the presence of $K_2CO_3$.

Non-limiting Example

Preparation of Ethyl 2-[4-(para-chlorobenzoyl)-phenoxy]-propionate 0.75 mole (175 g) of 4'-chloro-4-hydroxy-benzophenone, 1.5 l of methylisobutylketone, 0.975 mole (134 g) of $K_2CO_3$ and 0.8 mole (145 g) of ethyl 2-bromopropionate are placed in a 2-liter flask. The mixture is heated at reflux for 8 hours with vigorous agitation whereupon the reaction mixture is cooled and filtered on a Büchner funnel. The solvent is then evaporated under vacuum and the residue distilled; the desired ester is recovered at 198° to 201° C. under 0.1 mm of mercury. Yield 190 g (76%).

The reaction (method Ac3) using 2-hydroxy-isobutyric acid, involves a dehydration which can be carried out in solution of DMF or toluene either (i) in an acid medium ($H_2SO_4$, paratoluene-sulphonic acid) or (ii) in an alkaline medium, with mechanism (i) being preferred. This method is derived from the description of German Patent Application DOS No. P 2112 272 5.

In the preferred method, which uses acetone-chloroform, the following acid is obtained as an intermediate compound:

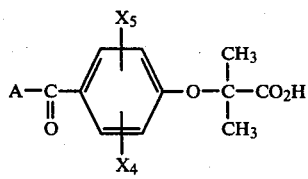

This is then converted to an amide or ester as the case may be.

The conversion of the acids of formula I into amides and esters is given below in a general manner:

Conversion into amide or ester (tertiary alcohol, alcohol amide or 3-pyridylmethanol).

First the acid chloride is synthetised from the acid and phosphorus pentachloride until cold (0°-5° C.). The acid chloride is reacted with the amine or alcohol desired in the presence of a tertiary amine (triethylamine or pyridine) to neutralise the hydrochloric acid formed.

Non-limiting Example

Preparation of the amido-ester of formula

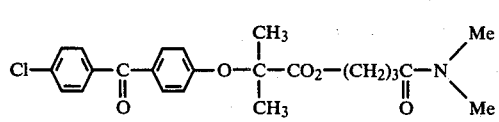

32 g (0.1 mole) of 2[4-(p-chlorobenzoyl)-phenoxy]-2-methylpropionic acid is suspended in 250 cc of dry toluene, and cooled in an ice bath. 20 g of phosphorous pentachloride is then added little by little. The reaction mixture is stirred for 2 hours at this temperature and when everything has dissolved, the toluene and the phosphorus oxychloride formed are evaporated off. The solid residue, which has a melting point of 80° C., is recrystallised from hexane: it is the acid chloride. To purify this crude material, it is re-dissolved in the minimum quantity of toluene and 0.1 mole of pyridine (8 g) and, slowly, 0.1 mole (13 g) of 4-hydroxy-N,N-dimethyl-butyramide is added. The reaction is completed by heating for 1 hour on a water bath at 50° C. Then the mixture is allowed to cool and the pyridinium hydrochloride filtered off. The filtered organic phase is washed with water, dried and decolorised and the solvent is evaporated off under vacuum. The desired ester crystallises. Yield 35 g (22%). Melting point 92° C.

Conversion into ester (using a secondary or primary alcohol)

Direct esterification is carried out, the esterification process being one which has particularly been investigated and adapted for use with a secondary alcohol. Accordingly, this original process can be used in the case of a primary alcohol with reaction kinetics which are definitely faster; this method consists in carrying out esterification with a relatively small amount of the chosen alcohol (1 to 1.5 liters of alcohol per 1 kg of acid of formula I and 0.6 kg of sulphuric acid per 1 kg of acid of formula I).

EXAMPLE

Preparation of 2-(4-(p-chlorobenzoyl)-phenoxy)-2-methylpropionic acid isopropyl ester 1 kg of the preceding acid is suspended in 1.5 l of isopropanol; 600 g of sulphuric acid is slowly added and the reaction mixture is refluxed for 12 hours. The mixture is allowed to cool, the ester crystallises, is carefully suction dried, is washed with 1% concentration soda while shaking, is suction dried again, and is recrystallised in 1.5 l of isopropanol in the presence of animal charcoal; the product which recrystallises is pure:

Weight=1.020 kg;
m.p.=80° C.;
Yield: 85%

Transformation into ester (with an amino alcohol or alcohol amide)

The reaction may of course be carried out with the acid chloride, but the preferred method is a transesterification starting from a simple ester (methyl ester for example) and the chosen aminoalcohol or alcohol amide. The catalyst may be sodium, a metal isopropylate (titanium isopropylate being preferred) or APTS.

Non-limiting Example

Preparation of Diethylaminoethyl 2-(p-benzoylphenoxy)-2-methylpropionate

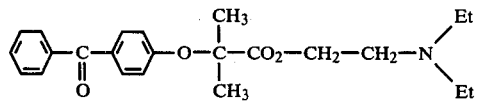

299 g (1 mole) of methyl 2-(p-benzoylphenoxy)-2-methylpropionate, 30 g of titanium isopropylate and 117 g (1 mole) of diethylaminoethanol are placed in a 500-cc flask. The reaction mixture is heated for 45 minutes at 120° C. (interior temperature) so as to distil off all the alcohol formed. The mixture is then allowed to cool and poured on to 10% hydrochloric acid in the presence of ether. The aqueous phase is made alkaline and then extracted with methylene chloride. The organic phase is carefully washed with water, then dried, decolorised and concentrated under vacuum. The residual oil is the desired ester. Yield 264 g, 69%. The maleate salt melts at 62° C.

For the preparation of hydroxyketones VII

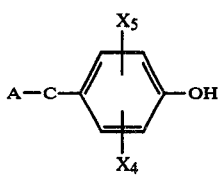

the common starting material for all the products prepared by the methods Ac contemplated are those obtained by one of the following two methods:

The first reaction scheme is carried out regardless of the A group

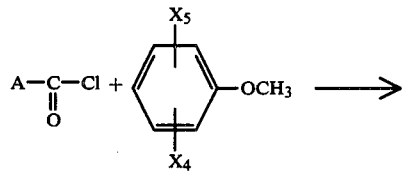

In the second method the reaction is carried out wherein A is the group

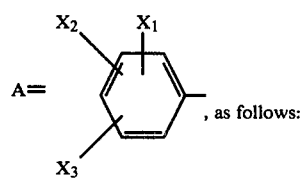, as follows:

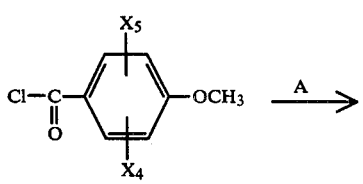

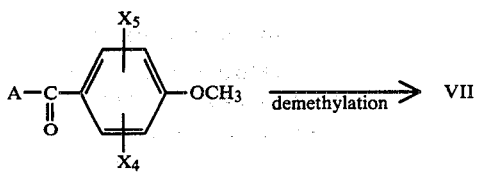

A similar technique has also been contemplated concerning the first step paragraph Aa. The second demethylation stage is conducted with 48% HBr or aluminium chloride of pyridinium hydrochloride.

Non-limiting Example

Preparation of 4'-chloro-4-hydroxybenzophenone 510 g of aluminium chloride (3.82 M), then 3.5 l of dry methylene chloride, and, slowly, 430 g (4 M) of anisole are added to a 5-liter flask; the flask is cooled to maintain the temperature at about 25° C., and 600 g (3.44 M) of 4-chlorobenzoyl chloride is then added dropwise; the reaction mixture is next heated 6 hours under reflux, is left to cool to about 25° C., and the reaction mixture is poured onto 5 kg of ice and 0.5 l of concentrated HCl; the mixture is stirred well during this hydrolysis; the methylene chloride phase is decanted, washed once with water, and transferred to another 5-liter vessel. The methylene chloride is removed by evaporation and replaced in the flask by 2 l of chlorobenzene; a Dean-Stark apparatus is connected and the reaction mixture is refluxed to dehydrate the medium; when this operation is complete the mixture is cooled to approximately 50° C. and 800 g (6 M) of aluminium chloride is added; the reaction mixture is heated 1 hour 30 minutes under reflux (very gentle reflux), and demethylation proceeds rapidly; the reaction mixture is cooled and poured onto 6 kg of ice and 0.5 l of concentrated HCl; the mixture is stirred for 1 hour 30 minutes and the precipitate is dried; the latter is washed with water, with methylene chloride, and then dried:

Weight=720 g;
m.p.=178° C.;
Yield: 90%

$\beta$-Methods using an organometallic compound

It is possible to use the methods previously described in paragraph Ab or in paragraph Ba1 below (organolithium compounds). The following reaction scheme and non-limiting example are given to illustrate this method.

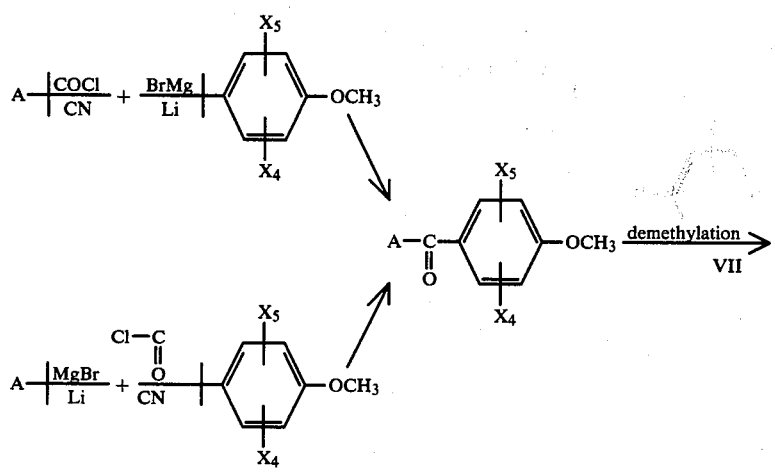

Non-limiting Example

Preparation of 3'-trifluoromethyl-4-hydroxybenzophenone 0.15 mole (90 cc) of n-butyl lithium is cooled to −70° C. in ether. 34 g (0.1 mole) of 3-trifluoromethyl-bromobenzene is added drop by drop. The mixture is stirred for 5 minutes at −70° C. after the addition and, still at that temperature 23 g (0.15 mole) of sodium 4-methoxyphenylcarboxylate is added. The temperature is allowed to rise to the ambient and the mixture is then stirred for 16 hours at ambient temperature. The mixture is hydrolysed and extracted with ether and the ethereal phase is washed with water, dried, decolorised, and concentrated. There remains an oil which crystallises from hexane. Yield 32 g (76%). Melting point 65° C.

To carry out demethylation, the 32 g of the oil obtained in the precedin paragraph is refluxed for 30 minutes with 170 g of pyridinium hydrochloride. The mixture is allowed to cool, taken up in 10% hydrochloric acid and extracted with ether and the ethereal phase is extracted with 2 N soda than acidified with HCl. The product is precipitated. Yield 28 g. Melting Point 129° C.

γ—Method using a bromine derivative

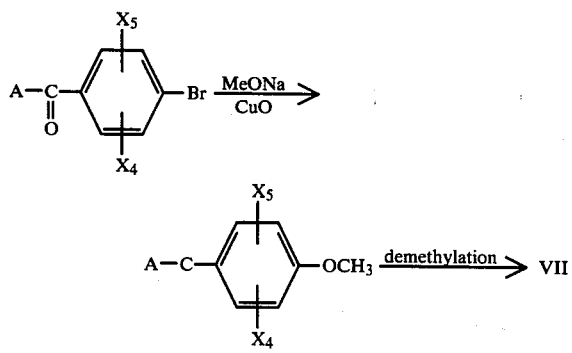

Non-limiting Example

Preparation of 4-(α-thenoyl)-phenol

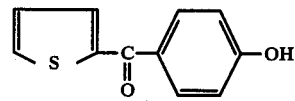

A mixture of 20 g of 4-(α-thenoyl)-bromobenzene, 4 g of anhydrous cupric oxide and 10 g of sodium methoxide in 130 cc of anhydrous methanol is refluxed for 20 hours in a 250 cc flask. Subsequently the mixture is filtered and the methanol evaporated off, resulting in a yield of 15.3 g of 4-(α-thenoyl)-anisole. (Melting point 73° C.). This is demethylated with aluminium chloride in chlorobenzene as described above and 13 g of the desired phenol is obtained. Yield 85%. Melting point 86° C.

δ—Particular Instance

Production of

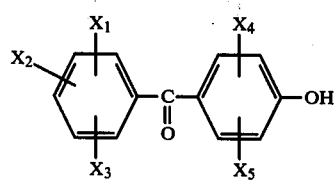

where at least 2 substituents are methoxy.

In the first stage the ether chosen need not be a methyl ether and a t-butyl of the formula

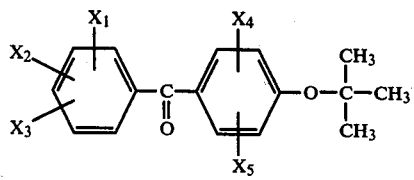

is synthesised by one of the three preceding methods α, β or γ from which the hydroxyketone VII methoxylated at $X_1$, $X_2$ or $X_3$ can easily be regenerated (by APTS for example).

ε Methods not involving the intermediate ether

The OH residue of VII is introduced (1) directly by

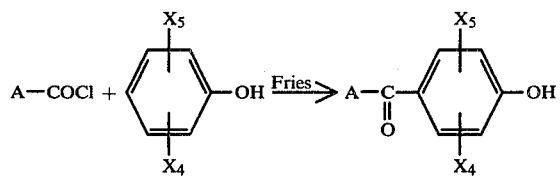

This method gives excellent yields when A is alkyl.

(2) by an intermediate sulphonic acid

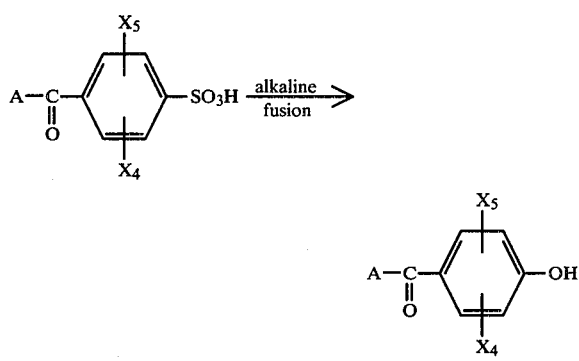

(3) by an intermediate nitro compound

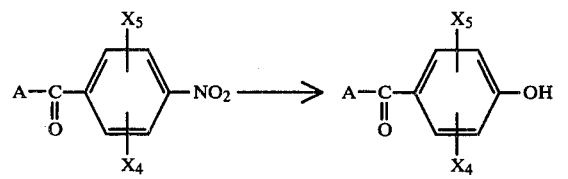

This last method is generally interesting and on the other hand of particular interest for preparing a final product of formula I having a hydroxy substituent (for example $X_1$, $X_2$ or $X_3$ in radical A). This method has been used several times and it is illustrated below by two examples.

Non-limiting Example

Preparation of 4'-chloro-4-hydroxybenzophenone 250 cc of DMSO and 4.8 g sodium hydride are placed in a 500 cc flask and heated at 70° C. for 1 hour, by which time the solution has become clear. A solution of 24.2 g (0.2 mole) of benzaldoxime in 100 cc of DMSO is then added drop by drop. The solution is maintained at 70° C. for 1 hour, then allowed to cool to 15° C. A solution of 26 g (0.1 mole) of 4'-chloro-4-nitrobenzophenone in 150 cc of DMSO is then added. The reaction mixture is stirred for 20 hours at ambient temperature and then poured into acidulated water. The mixture is extracted with ether and then with ether containing 2 N caustic soda. On acidification the product is precipitated. Yield 15 g (65%). Melting point 178° C.

Non-limiting Example

Preparation of Isopropyl 2-[4-(4-hydroxybenzoyl)-phenoxy]-2-methylpropionate

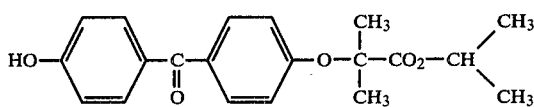

The mode of operation is identical with the above; however, to avoid the saponification of the ester function of the starting material, which has the formula

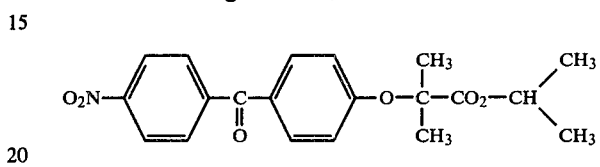

the latter is dissolved in DMSO at 8° C. and the sodium salt of benzaldoxime suspended in DMSO, (first stage in the preparation) is added little by little with a spatula. The treatment is identical with that indicated in the preceding example and the desired product is obtained in a yield of 76%, melting point 124° C.

In Table IV below all the hydroxyketones used, and their mode of operation are set out: it is also indicated which of them are novel compounds.

B—Access to compounds of formula I via products having a potential carboxylic acid group The potential carboxylic acid group chosen is an "isobutyric" aldehyde which is protected as an acetal:

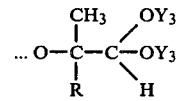

where Y is $C_{1-4}$ alkyl, preferably $C_2H_5$, so that the following processes (a) and (b) can be employed:

(a) Processes employing an organo-metallic compound

The property which organo-metallic compounds have, depending on their nature, of forming ketones when they are reacted with a nitrile, an acid chloride or a carboxylic acid salt, is utilised: ketones of the formula:

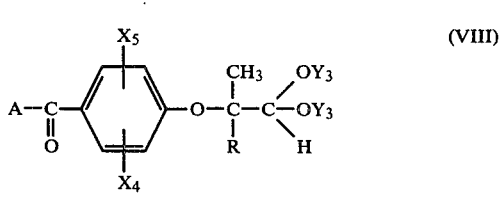

(VIII)

are thus obtained as intermediates. The aldehyde is regenerated by hydrolysis of the acetal VIII and is oxidised to the acid, the acid then being subjected to esterification or amidation reactions.

METHOD Pa1

Use of an organo-lithium compound

The reaction mechanisms are summarized hereinafter (with $Y_3$ and $C_2H_5$)

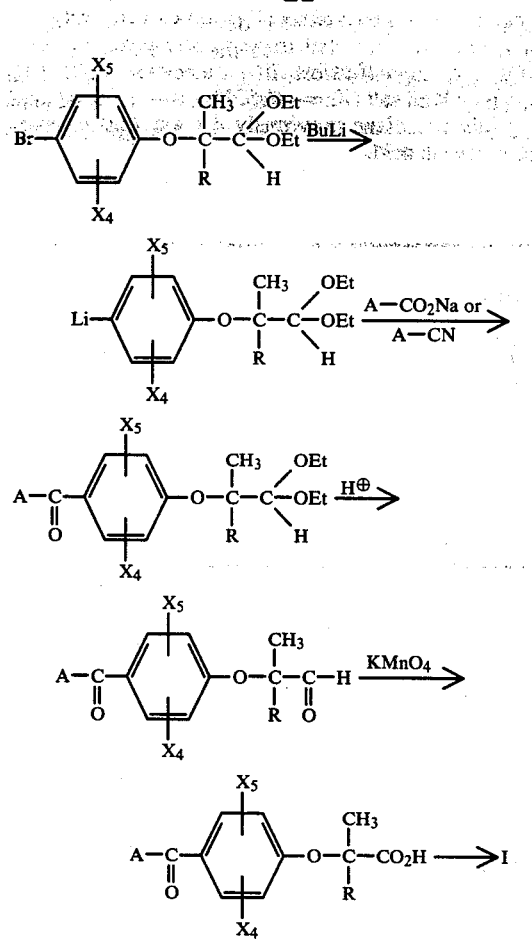

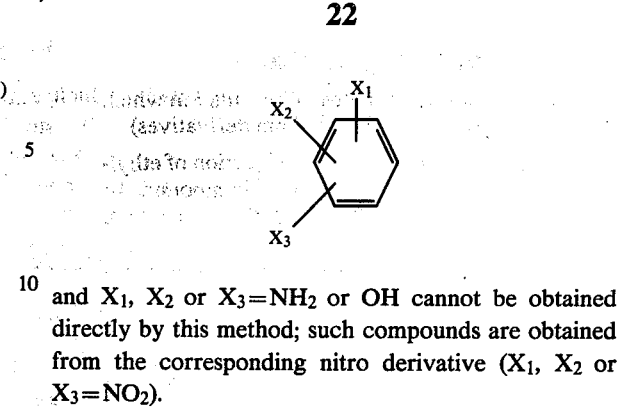

and $X_1$, $X_2$ or $X_3=NH_2$ or OH cannot be obtained directly by this method; such compounds are obtained from the corresponding nitro derivative ($X_1$, $X_2$ or $X_3=NO_2$).

METHOD Ba2

Use of an organo-magnesium compound

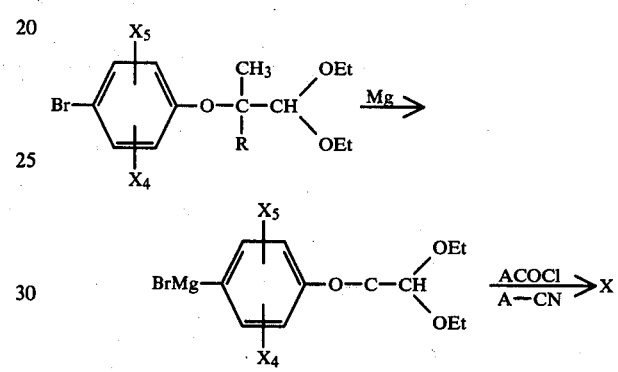

The organo-magnesium compound may be obtained from IX either directly (Mg in ether or THF), or by exchange with $CH_3MgI$. Condensation of this organo-magnesium compound with an acid chloride or a nitrile is subject to the same comments as those expressed at Ab. Of course, the compounds where X or $X_1$, $X_2$ or $X_3=OH$ or $NH_2$ can only be obtained from a corresponding nitro derivative.

(b) Processes employing a "hydroxyketone"

This simply involves condensing a hydroxyketone with a brominated acetal in alkaline medium according to the reaction

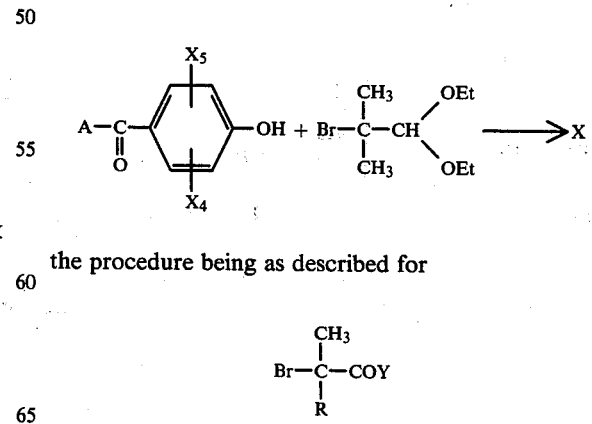

the procedure being as described for

The compound IX is lithiated with Bu-Li in ether at a temperature between $-70°$ C. and $0°$ C., and the product thus obtained is reacted with the sodium salt of the acid ACOOH (or the corresponding nitrile) at ambient temperature; the ketone X thus obtained is treated in an acid medium and liberates a ketone-aldehyde which is oxidised with potassium permanganate, the acid obtained being esterified or amidated in accordance with the processes described previously. The compounds IX are novel and are obtained conventionally in accordance with the following reaction scheme:

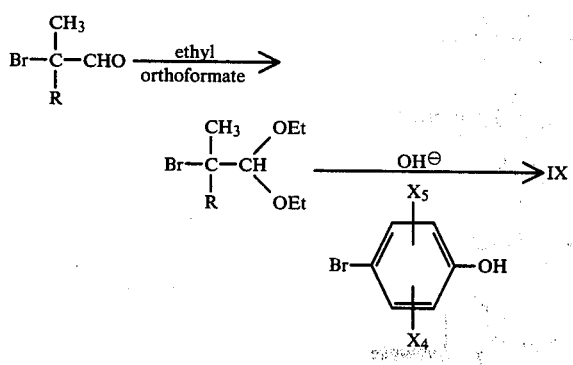

As has already been stated above (at Ab3), compound X in which A is at Ac, the condensation product X thus obtained being treated as mentioned above to give the compound I.

Non-limiting Example

Method for preparing compounds of formula I in which $X_0$ is $-O(CH_2)_2-O-$ (1,3-dioxolane derivatives)

These compounds are obtained by the action of ethyleneglycol in the presence of APTS on compounds of formula I in which $X_0$ is oxygen and Y is other than hydrogen; the 1,3-dioxolane derivatives are obtained. They cannot be converted to the corresponding acids (Y=OH) by saponification. It is necessary in fact to stop at the alkali salt ($X_0 = -O(CH_2)_2O-$ because acid cleaves the dioxolane previously formed and regenerates the ketone acid.

TABLE I

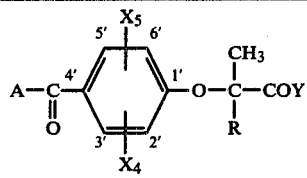

| Product | Code No. | A | $X_4$ | $X_5$ | R | Y | Melting point (°C.) or other physical characteristic if indicated |
|---|---|---|---|---|---|---|---|
| A-1 | 88 | phenyl | H | H | $CH_3$ | OH | 130 |
| A-2 | 153 | Cl—phenyl | H | H | $CH_3$ | OH | 185 |
| A-3 | 162 | Cl—phenyl | H | H | $CH_3$ | $OCH_3$ | 89 |
| A-4 | 163 | Cl—phenyl | H | H | $CH_3$ | $OC_2H_5$ | 79 |
| A-5 | 170 | Cl—phenyl | H | H | $CH_3$ | —N(piperidine) | 160 |
| A-6 | 171 | Cl—phenyl | H | H | $CH_3$ | —N(morpholine) | 148 |
| A-7 | 178 | Cl—phenyl | H | H | $CH_3$ | $OCH(CH_3)_2$ | 80 |
| A-8 | 180 | phenyl | H | H | $CH_3$ | $OCH_3$ | 58 |
| A-9 | 186 | phenyl | H | H | $CH_3$ | $OC_2H_5$ | 87 |
| A-10 | 190 | phenyl | H | H | $CH_3$ | $-O-CH(CH_3)_2$ | 84 |
| A-11 | 208 | phenyl | H | H | $CH_3$ | $-O(CH_2)_2-N$(piperidine), fumarate | 100 |
| A-12 | 209 | phenyl | H | H | $CH_3$ | $-O(CH_2)_2-N$(morpholine), fumarate | 118 |
| A-13 | 211 | phenyl | H | H | $CH_3$ | $-O(CH_2)_2-N$(azepane), fumarate | 115 |
| A-14 | 212 | phenyl | H | H | $CH_3$ | $-O(CH_2)_2-N(Et)_2$, maleate | 62 |
| A-15 | 217 | Cl—phenyl | H | H | $CH_3$ | $-O-$phenyl$-Cl$ | 135 |
| A-16 | 229 | Cl—phenyl | H | H | $CH_3$ | $-O(CH_2)_2-N$(azepane), fumarate | 122 |
| A-17 | 230 | Cl—phenyl | H | H | $CH_3$ | $-O(CH_2)_2-N(Et)_2$, HCl | 104 |

TABLE I-continued

A—C(=O)—[phenyl with X5 at 5', X4 at 3', 2', 6' positions, O—C(CH3)(R)—COY at 1']

| Product | Code No. | A | X₄ | X₅ | R | Y | Melting point (°C.) or other physical characteristic if indicated |
|---|---|---|---|---|---|---|---|
| A-18 | 231 | 4-Cl-C₆H₄— | H | H | CH₃ | —O(CH₂)₂—N(pyrrolidine), fumarate | 116 |
| A-19 | 238 | 4-Cl-C₆H₄— | H | H | CH₃ | —O—CH₂—(pyridyl), HCl | 144 |
| A-20 | 239 | 4-Cl-C₆H₄— | H | H | CH₃ | —O(CH₂)₂—N(morpholine), HCl | 145 |
| A-21 | 253 | 4-Cl-C₆H₄— | 3'-CH₃ | H | CH₃ | —O—CH(CH₃)₂ | Boiling point 220° C./0.01 mm Hg |
| A-22 | 259 | 4-Cl-C₆H₄— | H | H | CH₃ | —O(CH₂)₃—O₂C—C(CH₃)₂—O—C₆H₄—C(=O)—C₆H₄—Cl | oil |
| A-23 | 328 | C₆H₅— | H | H | CH₃ | —NH—(CH₂)₂N(Et)₂, fumarate | 176 |
| A-24 | 340 | C₆H₅— | H | H | CH₃ | —O—(CH₂)₂—N(piperidine), oxalate | 125 |
| A-25 | 384 | 4-Cl-C₆H₄— | H | H | CH₃ | —O—CH C₇H₁₄ | 90 |
| A-26 | 385 | 4-Cl-C₆H₄— | H | H | CH₃ | —O—C₁₂H₂₅ | 47 |
| A-27 | 386 | 4-Cl-C₆H₄— | H | H | CH₃ | —SEt | 49 |
| A-28 | 387 | 4-Cl-C₆H₄— | H | H | CH₃ | —N(Et)₂ | 117 |
| A-29 | 388 | 4-Cl-C₆H₄— | H | H | CH₃ | —OC₈H₁₇ | $n_{20}^D = 1.535$ |
| A-30 | 401 | 2,6-Cl₂-C₆H₃— | H | H | CH₃ | OH | 196 |
| A-31 | 402 | 2,6-Cl₂-C₆H₃— | H | H | CH₃ | —O—CH(CH₃)₂ | 115 |
| A-32 | 403 | 3-Cl-C₆H₄— | H | H | CH₃ | —O—CH(CH₃)₂ | 79 |
| A-33 | 404 | 4-Cl-C₆H₄— | H | H | CH₃ | OH | 155 |
| A-34 | 405 | 3,4-Cl₂-C₆H₃— | H | H | CH₃ | —O—CH(CH₃)₂ | 69 |

TABLE I-continued

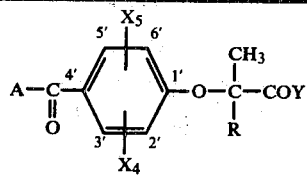

| Product | Code No. | A | X₄ | X₅ | R | Y | Melting point (°C.) or other physical characteristic if indicated |
|---|---|---|---|---|---|---|---|
| A-35 | 406 | 3-Cl-C₆H₄ | H | H | $CH_3$ | OH | 121 |
| A-36 | 507 | 4-Br-C₆H₄ | H | H | $CH_3$ | OH | 182 |
| A-37 | 512 | 4-Cl-C₆H₄ | 3'-$CH_3$ | 5'-$CH_3$ | $CH_3$ | —O—CH($CH_3$)₂ | 67 |
| A-38 | 517 | 4-Cl-C₆H₄ | 3'-$CH_3$ | 5'-$CH_3$ | $CH_3$ | OH | 92 |
| A-39 | 518 | 4-Br-C₆H₄ | H | H | $CH_3$ | —O—CH($CH_3$)₂ | 98 |
| A-40 | 573 | 4-$H_3CO$-C₆H₄ | H | H | $CH_3$ | OH | 144 |
| A-41 | 573A | 4-$H_3CO$-C₆H₄ | H | H | $CH_3$ | —O—CH($CH_3$)₂ | 95 |
| A-42 | 575 | 4-Cl-C₆H₄ | H | H | $CH_3$ | —OCH₂-(3-hydroxy-4-hydroxymethyl-2-methylpyridin-5-yl) | 130 |
| A-43 | 590 | 2-Cl-C₆H₄ | H | H | $CH_3$ | OH | 114 |
| A-44 | 602 | 2-$CH_3$-C₆H₄ | H | H | $CH_3$ | OH | 129 |
| A-45 | 606 | 4-$O_2N$-C₆H₄ | H | H | $CH_3$ | OH | 182 |
| A-46 | 606A | 4-$O_2N$-C₆H₄ | H | H | $CH_3$ | —O—CH($CH_3$)₂ | 120 |
| A-47 | 607 | 2,6-(CH₃)₂-C₆H₃ | H | H | $CH_3$ | OH | 126 |
| A-48 | 611 | 4-$H_2N$-C₆H₄ | H | H | $CH_3$ | —OCH($CH_3$)₂ | 120 |
| A-49 | 618 | 4-$H_2N$-C₆H₄ | H | H | $CH_3$ | OH | 158 |
| A-50 | 619 | 4-F-C₆H₄ | H | H | $CH_3$ | OH | 160 |
| A-51 | 627 | 4-HO-C₆H₄ | H | H | $CH_3$ | —OCH($CH_3$)₂ | 124 |
| A-52 | 634 | 4-HO-C₆H₄ | H | H | $CH_3$ | OH | 192 |
| A-53 | — | 4-F-C₆H₄ | H | H | $CH_3$ | —O—CH($CH_3$)₂ | 68 |

TABLE I-continued

Structure:
$$A-\underset{\underset{O}{\parallel}}{C}-\text{(phenyl with } X_4 \text{ at 3',} X_5 \text{ at 5')}-O-\underset{\underset{R}{|}}{\overset{\overset{CH_3}{|}}{C}}-COY$$

| Product | Code No. | A | X₄ | X₅ | R | Y | Melting point (°C.) or other physical characteristic if indicated |
|---|---|---|---|---|---|---|---|
| A-54 | 398 | Cl—C₆H₄— | H | H | H | OH | 146 |
| A-55 | 399 | Cl—C₆H₄— | H | H | H | OCH(CH₃)₂ | 97 |
| A-55 bis | 624 | Cl—C₆H₄— | 2'-CH₃ | 6'-CH₃ | CH₃ | OH | 120 |
| A-56 | 632 | Cl—C₆H₄— | H | H | CH₃ | OCH(CH₃)(C₂H₅) | 70 |
| A-57 | 643 | Cl—C₆H₄— | H | H | CH₃ | OC(CH₃)₃ | 77 |
| A-58 | 644 | Cl—C₆H₄— | H | H | CH₃ | OCH₂—(2,2-dimethyl-1,3-dioxolan-4-yl) | 176 |
| A-59 | — | Cl—C₆H₄— | H | H | CH₃ | OCH₂CH(OH)CH₂OH | $n_D^{20} = 1.5535$ |
| A-60 | 645 | Cl—C₆H₄— | H | H | CH₃ | O(CH₂)₂CON(CH₃)₂ | 90 |
| A-61 | 642 | 3-CF₃—C₆H₄— | H | H | CH₃ | OH | 108 |
| A-62 | 641 | 3-CF₃—C₆H₄— | H | H | CH₃ | OCH(CH₃)₂ | $n_D^{20} = 1.516$ |
| A-63 | — | 3,4,5-(H₃CO)₃—C₆H₂— | H | H | CH₃ | OH | 129 |
| A-64 | — | 3,4,5-(H₃CO)₃—C₆H₂— | H | H | CH₃ | OCH(CH₃)₂ | 38 |
| A-65 | — | 4-Cl-3-H₃CO—C₆H₃— | H | H | CH₃ | OH | — |
| A-66 | — | 4-Cl-3-H₃CO—C₆H₃— | H | H | CH₃ | OCH(CH₃)₂ | — |
| A-67 | 635 | H₃C—C(=O)—O—C₆H₄— | H | H | CH₃ | —OCH(CH₃)₂ | 85 |
| A-68 | 559 | (CH₃)₂—CH— | H | H | CH₃ | OH | — |
| A-69 | 538 | (CH₃)₂—CH— | H | H | CH₃ | OCH(CH₃)₂ | — |
| A-70 | 637 | Cl—C₆H₄— | H | H | CH₃ | —NH(CH₂)₂—N(Et)₂ | 64 |

TABLE I-continued

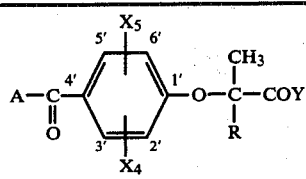

| Product | Code No. | A | X₄ | X₅ | R | Y | Melting point (°C.) or other physical characteristic if indicated |
|---|---|---|---|---|---|---|---|
| A-71 | 639 | Cl—C₆H₄— | H | H | CH₃ | —O—(CH₂)₃—CON(Me)₂ | 92 |
| A-72 | — | Cl—C₆H₄— | H | H | CH₃ | —O—CH(CH₃)CH₂CH₂CH₃ | 55 |
| A-73 | — | Cl—C₆H₄— | H | H | CH₃ | —O—CH(C₂H₅)₂ | 67 |
| A-74 | — | Br—C₆H₄— | H | H | CH₃ | —O—CH(CH₃)CH₂CH₃ | 82 |
| A-75 | — | Br—C₆H₄— | H | H | CH₃ | —O—C₈H₁₇ | 38 |
| A-76 | — | Br—C₆H₄— | H | H | CH₃ | —O—CH₂—(3-pyridyl), HCl | 114 |
| A-77 | — | Br—C₆H₄— | H | H | CH₃ | —O—(CH₂)₂—N(hexamethyleneimino), HCl | 138 |
| A-78 | — | Br—C₆H₄— | H | H | CH₃ | —N(morpholino) | 160 |
| A-79 | — | Br—C₆H₄— | H | H | CH₃ | —O—C₁₂H₂₅ | 37 |
| A-80 | — | Br—C₆H₄— | H | H | CH₃ | —O—(CH₂)₂—N(Et)₂, HCl | hygroscopic |
| A-81 | — | H₃CO—C₆H₄— | H | H | CH₃ | —O—(CH₂)₂—N(hexamethyleneimino), HCl | 125 |
| A-82 | 272 | C₆H₅— | H | H | H | —O—(CH₂)₂—N(morpholino), fumarate | 110 |
| A-83 | 391 | cyclohexyle | H | H | CH₃ | OH | 148 |
| A-84 | 390 | cyclohexyle | H | H | CH₃ | O—CH(CH₃)₂ | 67 |
| A-85 | — | 4-CH₃OC₆H₄ | H | H | CH₃ | O—C₁₂H₂₅ | 38 |
| A-86 | — | 4-CH₃OC₆H₄ | H | H | CH₃ | O—CH(CH₃)C₂H₅ | 74 |
| A-87 | — | 4-ClC₆H₄ | 2'-CH₃ | 6'-CH₃ | CH₃ | O CH(CH₃)₂ | 70 |

TABLE II

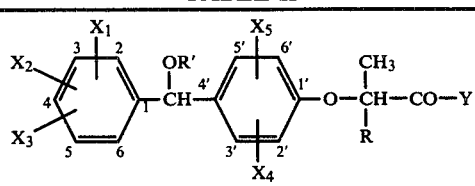

| Product | X₁ | X₂ | X₃ | X₄ | X₅ | R | R' | Y |
|---|---|---|---|---|---|---|---|---|
| B-1 (a) | 4-Cl | H | H | H | H | CH₃ | H | OCH(CH₃)₂ |
| B-2 (b) | 4-Cl | H | H | H | H | CH₃ | H | OH |
| B-3 (c) | 4-Cl | H | H | H | H | CH₃ | H | OH |
| B-4 (d) | 4-Cl | H | H | H | H | CH₃ | CH₃ | OCH(CH₃)₂ |
| B-5 | 4-Cl | H | H | H | H | CH₃ | COCH₃ | OCH(CH₃)₂ |
| B-6 | 4-Cl | H | H | H | H | CH₃ | H | OCH₃ |
| B-7 | 4-Cl | H | H | H | H | CH₃ | H | OC₂H₅ |

TABLE II-continued

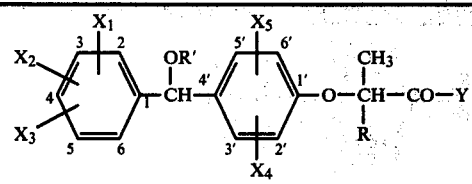

| Product | X₁ | X₂ | X₃ | X₄ | X₅ | R | R' | Y |
|---|---|---|---|---|---|---|---|---|
| B-8 | 4-Cl | H | H | H | H | CH₃ | H | —N(piperidine) |
| B-9 | 4-Cl | H | H | H | H | CH₃ | H | —N(morpholine) |
| B-10 | H | H | H | H | H | CH₃ | H | OH |
| B-11 | H | H | H | H | H | CH₃ | H | OCH₃ |
| B-12 | H | H | H | H | H | CH₃ | H | OC₂H₅ |
| B-13 | H | H | H | H | H | CH₃ | H | OCH(CH₃)₂ |
| B-14 | H | H | H | H | H | CH₃ | H | O(CH₂)₂—N(hexamethyleneimine), fumarate |
| B-15 | H | H | H | H | H | CH₃ | H | O(CH₂)₂—N(morpholine), fumarate |
| B-16 | H | H | H | H | H | CH₃ | H | O(CH₂)₂—N(piperidine), fumarate |
| B-17 | H | H | H | H | H | CH₃ | H | O(CH₂)₂—N(C₂H₅)₂, maleate |
| B-18 | 4-Cl | H | H | H | H | CH₃ | H | O—C₆H₄—Cl |
| B-19 | 4-Cl | H | H | H | H | CH₃ | H | O(CH₂)₂—N(hexamethyleneimine), fumarate |
| B-20 | 4-Cl | H | H | H | H | CH₃ | H | O(CH₂)₂N(C₂H₅)₂, HCl |
| B-21 | 4-Cl | H | H | H | H | CH₃ | H | OCH(CH₃)₂ |
| B-22 | 4-Cl | H | H | 3'-CH₃ | H | CH₃ | H | clyclooctyloxy |
| B-23 | 4-Cl | H | H | H | H | CH₃ | H | O(CH₂)₁₁CH₃ |
| B-24 | 4-Cl | H | H | H | H | CH₃ | H | O(CH₂)₇CH₃ |
| B-25 | 2-Cl | 6-Cl | H | H | H | CH₃ | H | OH |
| B-26 | 2-Cl | 6-Cl | H | H | H | CH₃ | CH₃ | OH |
| B-27 | 2-Cl | 6-Cl | H | H | H | CH₃ | H | OCH(CH₃)₂ |
| B-28 | 2-Cl | 6-Cl | H | H | H | CH₃ | CH₃ | OCH(CH₃)₂ |
| B-29 | 3-Cl | H | H | H | H | CH₃ | H | OH |
| B-30 | 3-Cl | H | H | H | H | CH₃ | CH₃ | OH |
| B-31 | 3-Cl | H | H | H | H | CH₃ | H | OCH(CH₃)₂ |
| B-32 | 3-Cl | 4-Cl | H | H | H | CH₃ | H | OH |
| B-33 | 3-Cl | 4-Cl | H | H | H | CH₃ | H | OCH(CH₃)₂ |
| B-34 (e) | 4-Br | H | H | H | H | CH₃ | H | OH |
| B-35 | 4-Br | H | H | H | H | CH₃ | H | OH |
| B-36 (f) | 4-Br | H | H | H | H | CH₃ | H | OCH(CH₃)₂ |
| B-37 | 4-Cl | H | H | 3'-CH₃ | 5'-CH₃ | CH₃ | H | OH |
| B-38 | 4-Cl | H | H | 3'-CH₃ | 5'-CH₃ | CH₃ | H | OCH(CH₃)₂ |
| B-39 (g) | 4-OCH₃ | H | H | H | H | CH₃ | H | OH |
| B-40 (h) | 4-OCH₃ | H | H | H | H | CH₃ | H | OCH(CH₃)₂ |
| B-41 | 2-Cl | H | H | H | H | CH₃ | H | OH |
| B-42 | 2-Cl | H | H | H | H | CH₃ | H | OCH(CH₃)₂ |
| B-43 | 2-CH₃ | H | H | H | H | CH₃ | H | OH |
| B-44 | 2-CH₃ | H | H | H | H | CH₃ | H | OCH(CH₃)₂ |
| B-45 | 4-NO₂ | H | H | H | H | CH₃ | H | OH |
| B-46 | 4-NO₂ | H | H | H | H | CH₃ | H | OH |
| B-47 | 2-CH₃ | 6-CH₃ | H | H | H | CH₃ | H | OH |
| B-48 | 4-NH₂ | H | H | H | H | CH₃ | H | OH |
| B-49 | 4-NH₂ | H | H | H | H | CH₃ | H | OCH(CH₃)₂ |
| B-50 | 4-F | H | H | H | H | CH₃ | H | OH |
| B-51 | 4-F | H | H | H | H | CH₃ | H | OCH(CH₃)₂ |
| B-52 | 4-OH | H | H | H | H | CH₃ | H | OH |

TABLE II-continued

| Product | X₁ | X₂ | X₃ | X₄ | X₅ | R | R' | Y |
|---|---|---|---|---|---|---|---|---|
| B-53 | 4-OH | H | H | H | H | CH₃ | H | OCH(CH₃)₂ |
| B-54 | 4-Cl | H | H | H | H | H | H | OH |
| B-55 | 4-Cl | H | H | H | H | H | H | OCH(CH₃)₂ |
| B-56 | 4-Cl | H | H | H | H | CH₃ | H | OCH(CH₃)(C₂H₅) |
| B-57 | 4-Cl | H | H | H | H | CH₃ | CH₃ | OCH(CH₃)(C₂H₅) |
| B-58 | 4-Cl | H | H | H | H | CH₃ | H | OC(CH₃)₃ |
| B-59 | 4-Cl | H | H | H | H | CH₃ | H | OCH₂CHOHCH₂OH |
| B-60 | 4-Cl | H | H | H | H | CH₃ | H | O(CH₂)₂CON(CH₃)₂ |
| B-61 | 3-CF₃ | H | H | H | H | CH₃ | H | OH |
| B-62 | 3-CF₃ | H | H | H | H | CH₃ | H | OCH(CH₃)₂ |
| B-63 | 3-OCH₃ | 4-OCH₃ | 5-OCH₃ | H | H | CH₃ | H | OH |
| B-64 | 3-OCH₃ | 4-OCH₃ | 5-OCH₃ | H | H | CH₃ | H | OCH(CH₃)₂ |
| B-65 | 3-OCH₃ | 4-Cl | H | H | H | CH₃ | H | OH |
| B-66 | 3-OCH₃ | 4-Cl | H | H | H | CH₃ | H | OCH(CH₃)₂ |

Notes:
(a) : $n_D^{20} = 1.5428$;
(b) : M.P. = 132° C.;
(c) : M.P. = 99° C.;
(d) : $n_D^{20} = 1.5532$;
(e) : M.P. = 122° C.;
(f) : $n_D^{20} = 1.550$;
(g) : M.P. = 120° C.;
(h) : $n_D^{20} = 1.543$.

TABLE III

| Product | Code No. | Z | X₄ | X₅ | R | Y | M.P. (°C.) |
|---|---|---|---|---|---|---|---|
| C-1 | — | 4-Cl-C₆H₄-CH(O-)(O-) (cyclic acetal) | H | H | CH₃ | OK | — |
| C-2 | — | 4-Cl-C₆H₄-CH(O-)(O-) (cyclic acetal) | H | H | CH₃ | OCH(CH₃)₂ | — |
| C-3 | 574 | 5-Cl-thiophene-2-CO— | H | H | CH₃ | OH | 162 |
| C-4 | — | 5-Cl-thiophene-2-CO— | H | H | CH₃ | OCH(CH₃)₂ | 67 |
| C-5 | — | 5-Br-thiophene-2-CO— | H | H | CH₃ | OH | — |
| C-6 | — | 5-Br-thiophene-2-CO— | H | H | CH₃ | OCH(CH₃)₂ | — |

TABLE III-continued

Structure:

$$Z-\underset{X_4}{\overset{X_5}{\text{C}_6\text{H}_3}}-O-\underset{R}{\overset{CH_3}{C}}-COY$$

| Product | Code No. | Z | $X_4$ | $X_5$ | R | Y | M.P. (°C.) |
|---|---|---|---|---|---|---|---|
| C-16 | 640 | (CH$_3$)$_2$CH-O$_2$C-C(CH$_3$)$_2$-O-C$_6$H$_4$-CO- | H | H | CH$_3$ | OCH(CH$_3$)$_2$ | 72 |
| C-7 | 491 | 2-thienyl-CO- | H | H | CH$_3$ | OH | 156 |
| C-8 | 493 | 2-thienyl-CO- | H | H | CH$_3$ | OCH(CH$_3$)$_2$ | 63 |
| C-9 | 515 | 2-furyl-CO- | H | H | CH$_3$ | OH | 131 |
| C-10 | — | 2-furyl-CO- | H | H | CH$_3$ | OCH(CH$_3$)$_2$ | — |
| C-11 | — | 5-Br-2-furyl-CO- | H | H | CH$_3$ | OH | — |
| C-12 | 541 | 5-Br-2-furyl-CO- | H | H | CH$_3$ | OCH(CH$_3$)$_2$ | 72 |
| C-13 | 612 | 2-C$_2$H$_5$-benzofuran-3-yl-CO- | H | H | CH$_3$ | OH | 132 |
| C-14 | — | 2-C$_2$H$_5$-benzofuran-3-yl-CO- | H | H | CH$_3$ | OCH(CH$_3$)$_2$ | $n_D^{20} = 1.5455$ |
| C-15 | — | HO$_2$C-C(CH$_3$)$_2$-O-C$_6$H$_4$-CO- | H | H | CH$_3$ | OH | 185 |

TABLE IV

Structure:

$$A-\underset{O}{\overset{}{C}}-\underset{X_4}{\overset{X_5}{\text{C}_6\text{H}_3}}-OH$$

| A | $X_4$ | $X_5$ | M.P. (°C.) | Mode of preparation chosen |
|---|---|---|---|---|
| (CH$_3$)$_2$CH- | H | H | 51 | $\epsilon_1$ |
| cyclohexyl | H | H | 98 | $\alpha$ |
| phenyl | H | H | 133 | $\alpha$ |
| 4-Cl-C$_6$H$_4$- | H | H | 178 | $\alpha$ |
| 4-Cl-C$_6$H$_4$- | 2-CH$_3$ | 6-CH$_3$ | 140 | $\alpha$ |
| 4-Cl-C$_6$H$_4$- | 2-CH$_3$ | H | 114 | $\epsilon_1$ |

TABLE IV-continued

| A | X4 | X5 | M.P. (°C.) | Mode of preparation chosen |
|---|---|---|---|---|
|  3-Cl-phenyl | H | H | 120 | α |
|  2-Cl-phenyl | H | H | 164 | α |
|  3,4-diCl-phenyl | H | H | 178 | α |
| *  2,6-diCl-phenyl | H | H | 208 | α |
| Br—— | H | H | 192 | α |
| F—— | H | H | 168 | α |
| H3CO—— | H | H | 165 | ε3 |
|  2-CH3-phenyl | H | H | 104 | α |
| *  2,6-diCH3-phenyl | H | H | 155 | α |
| O2N—— | H | H | 190 | α |
|  3-CF3-phenyl | H | H | 139 | β |
|  3-OHC-phenyl | H | H | 98 | β |
| *  furyl-CH3 | H | H | 164 | β |
| *  Br-furyl | H | H | 190 | β |
|  Cl-thienyl | H | H | 139 | α,γ |
|  benzofuryl-C2H5 | H | H | 124 | α |
| thienyl | H | H | 88 | α,γ |
| *4-chlorophenyl | 3-CH3 | 5-CH3 | 98 | α |

Note:
* New compounds

I claim:
1. A compound of the formula:

$$A-\underset{X_o}{\overset{\parallel}{C}}-\underset{X_4}{\overset{X_5}{\underset{}{\bigcirc}}}-O-\underset{R}{\overset{CH_3}{\underset{|}{C}}}-CO-Y \quad (II)$$

wherein
A represents 2-methylphenyl, 2,6-dimethylphenyl, 4-ethylphenyl, 4-methoxyphenyl, 3,4,5-trimethoxyphenyl, 4-nitrophenyl, 4-aminophenyl, 4-trifluoromethylphenyl, 3-trifluoromethylphenyl or 4-chloro-3-methoxyphenyl;
R, $X_4$ and $X_5$ are the same or different and represent hydrogen or $C_{1-4}$alkyl;
Y represents OH or $C_{1-12}$alkoxy; and
$X_o$ represents oxygen if Y is OH or represents oxygen or the —O—CH$_2$—CH$_2$—O— group if Y is $C_{1-12}$alkoxy; or an acid addition thereof.
2. The compound as defined in claim 1 wherein R is CH$_3$, $X_4$ and $X_5$ are hydrogen and $X_o$ is oxygen.
3. A pharmaceutical composition for the treatment of hyperlipaemia comprising a therapeutically active amount of a compound as claimed in claim 1 or a nontoxic acid-addition salt thereof, and a physiologically acceptable pharmaceutical excipient.
4. Diethylaminoethyl 2-[(4-benzoyl)-phenoxy]-2-methylpropionate.
5. Isopropyl 2-[4-(p-hydroxybenzoyl)-phenoxy]-2-methylpropionate.
6. Isopropyl 2-[4-(p-nitrobenzoyl)-phenoxy]-2-methylpropionate.

* * * * *